(12) United States Patent
Turcott et al.

(10) Patent No.: US 7,653,434 B1
(45) Date of Patent: Jan. 26, 2010

(54) AUTONOMOUS SENSOR MODULES FOR PATIENT MONITORING

(75) Inventors: Robert G. Turcott, Mountain View, CA (US); Michael K. Fang, Mountain View, CA (US); Timothy A. Fayram, Gilroy, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 541 days.

(21) Appl. No.: 10/913,942

(22) Filed: Aug. 5, 2004

(51) Int. Cl.
*A61N 1/39* (2006.01)

(52) U.S. Cl. ........................................... 607/5
(58) Field of Classification Search ................ 607/1–9, 607/30–33
See application file for complete search history.

(56) References Cited

U.S. PATENT DOCUMENTS

| | | | |
|---|---|---|---|
| 5,282,841 A | 2/1994 | Szyszkowski ............... 607/36 |
| 5,313,953 A | 5/1994 | Yomtov et al. .............. 128/696 |
| 5,404,877 A | 4/1995 | Nolan et al. ................ 128/671 |
| 5,411,031 A | 5/1995 | Yomtov ...................... 128/706 |
| 5,470,435 A | 11/1995 | Rushmere et al. ......... 162/181.6 |
| 5,480,416 A | 1/1996 | Garcia et al. ................. 607/36 |
| 5,674,260 A | 10/1997 | Weinberg .................... 607/36 |
| 5,741,313 A | 4/1998 | Davis et al. .................. 607/36 |
| 5,769,874 A | 6/1998 | Dahlberg ..................... 607/36 |
| 5,814,091 A | 9/1998 | Dahlberg et al. ............. 607/36 |
| 5,904,708 A | 5/1999 | Goedeke ...................... 607/18 |
| 6,026,325 A | 2/2000 | Weinberg et al. ............ 607/36 |
| 6,190,324 B1 | 2/2001 | Kieval et al. ................ 600/483 |
| 6,277,078 B1 | 8/2001 | Porat et al. .................. 600/486 |
| 6,308,101 B1 * | 10/2001 | Faltys et al. ................. 607/57 |
| 6,324,428 B1 | 11/2001 | Weinberg et al. ............ 607/36 |
| 6,472,991 B1 * | 10/2002 | Schulman et al. ......... 340/995.1 |
| 6,477,406 B1 | 11/2002 | Turcott ....................... 600/518 |
| 6,480,733 B1 | 11/2002 | Turcott ....................... 600/516 |
| 6,529,771 B1 | 3/2003 | Kieval et al. ................ 600/509 |
| 6,645,143 B2 | 11/2003 | VanTassel et al. ........... 600/300 |
| 6,652,464 B2 | 11/2003 | Schwartz et al. ............ 600/486 |
| 6,714,811 B1 | 3/2004 | Padmanabhan et al. ..... 600/509 |
| 6,736,770 B2 | 5/2004 | Leysieffer et al. ............. 600/25 |
| 7,096,064 B2 * | 8/2006 | Deno et al. .................... 607/9 |
| 2003/0036776 A1 * | 2/2003 | Foster et al. ................... 607/9 |

FOREIGN PATENT DOCUMENTS

| | | |
|---|---|---|
| EP | 0 554 208 A2 | 1/1993 |
| EP | 0 941 695 A2 | 1/1993 |
| EP | 0 941 695 A3 | 1/1993 |
| EP | 0 941 695 B1 | 1/1993 |
| EP | 1 216 655 A1 | 12/2001 |
| WO | WO 99/47205 | 9/1999 |
| WO | WO 00/62860 | 10/2000 |
| WO | WO 00/64336 | 11/2000 |

OTHER PUBLICATIONS

US 6,359,771, 03/2002, Muse et al. (withdrawn)

* cited by examiner

*Primary Examiner*—George R Evanisko
*Assistant Examiner*—Rex Holmes
(74) *Attorney, Agent, or Firm*—Steven M. Mitchell; Theresa A. Takeuchi

(57) ABSTRACT

Embodiments of the present invention relate to implantable sensors for obtaining hemodynamic data and/or physiologic data. More specifically, embodiments of the present invention enable additional sensing hardware to be added into implantable devices more quickly and less expensively. Additionally, embodiments of the present invention enable such adding of additional sensing hardware with little or no effect on the conventional functions of the implantable device to which the sensor hardware is being added.

11 Claims, 8 Drawing Sheets

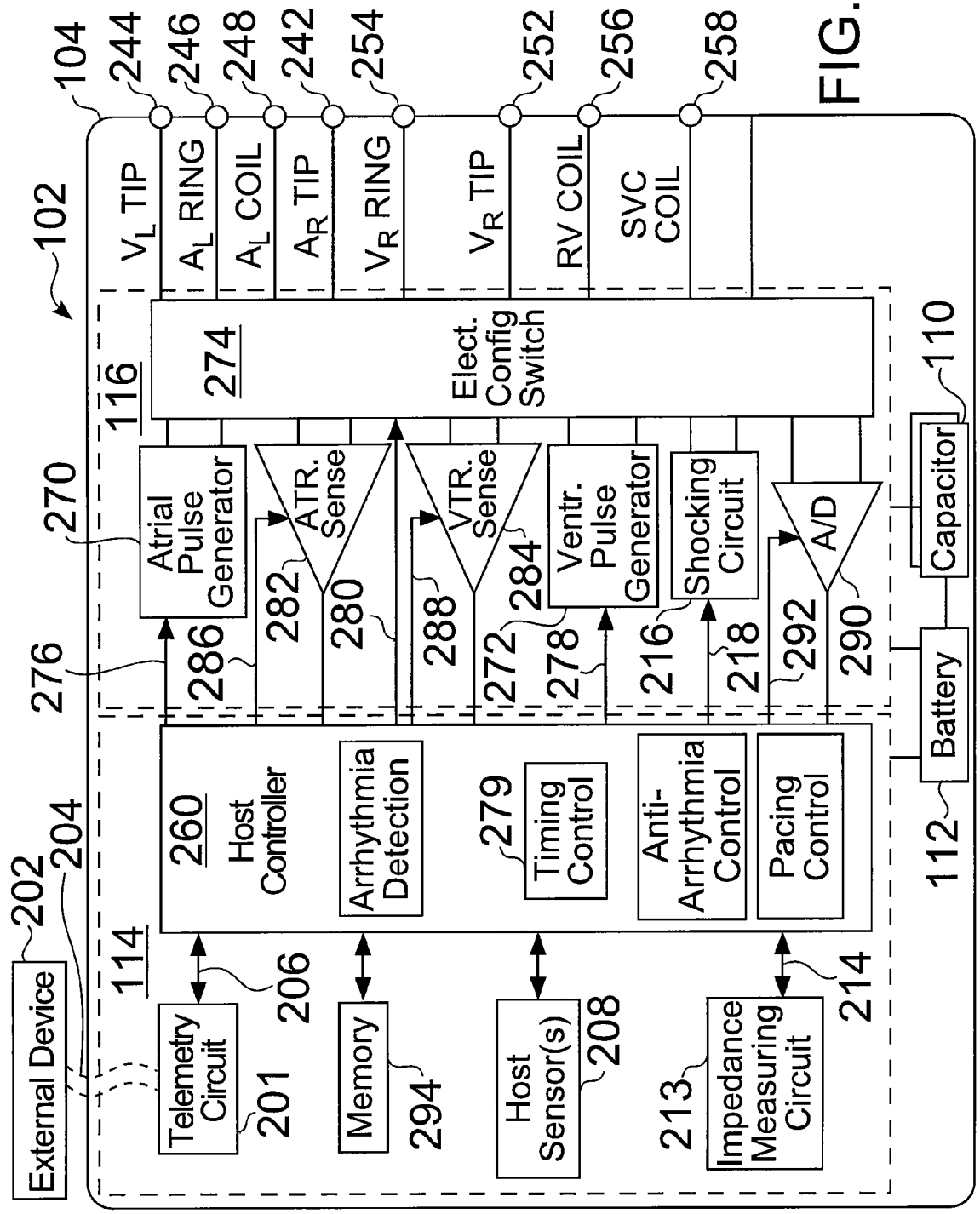

AUTONOMOUS SENSOR MODULES FOR PATIENT MONITORING

FIELD OF THE INVENTION

Embodiments of the present invention relate to implantable medical devices that include sensors for obtaining hemodynamic and/or physiologic data.

BACKGROUND OF THE INVENTION

Implantable medical devices of the type having electrical circuit components are well known in the medical arts. In one particularly common form, the implantable device is an implantable cardioverter-defibrillator (ICD), a pacemaker, or a combination thereof, having an appropriate electrical power supply and related control circuitry for use in electrically stimulating a patient muscle, such as the heart. Such a device commonly includes a hermetically sealed case or housing within which a power supply and control circuitry are placed. Additionally, one or more conductive leads will typically extend from the housing to a selected muscle structure within a patient.

Recently, there is the desire to chronically implant more physiological sensors within a patient to monitor various hemodynamic functions of the patient. If the patient already requires an implantable device, such as an ICD or pacemaker (referred to collectively hereafter as an implantable stimulation device), it is preferably to integrate any additional physiological sensors into the implantable stimulation device, so as to minimize the number of implants. Such sensors can include, for example, optoelectronic sensors that are useful for producing photoplethysmography signals and for obtaining measures of oxygen saturation using pulse oximetry. Other types of sensors include, but are not limited to, acoustic sensors that can measure heart sounds, temperature transducers, impedance sensors, electro-chemical sensors and ultrasound transducers.

Integrating additional sensing hardware into an implantable device increases the development and regulatory costs of the device. For can-based devices, such as ICDs and pacemakers, some of this cost is due to the need to redesign the layout of the internal components in order to accommodate the volume occupied by the additional sensor hardware. Additionally, providing signal connections, data management, and telemetry requires changes to device electronics, software and/or firmware. There are also additional burdens to Quality Assurance to verify that the additional sensor hardware does not compromise the conventional functions of the implantable device. For example, the power requirements of the sensor hardware may be such that it reduces the battery life of an ICD to an unacceptable level.

It would be desirable if additional sensing hardware can be integrated into implantable devices more quickly and less expensively. Further, it would be desirable if the affects on the conventional functions of implantable devices are reduced, and preferably minimized.

SUMMARY OF THE INVENTION

Embodiments of the present invention relate to implantable sensors for obtaining hemodynamic data and/or physiologic data. More specifically, embodiments of the present invention enable additional sensor hardware to be added to implantable devices more quickly and less expensively. Additionally, embodiments of the present invention enable such adding of additional sensor hardware with little or no effect on the conventional functions of the implantable device to which the sensor hardware is being added.

An implantable device according to specific embodiments of the present invention includes a host subsystem and a sensor subsystem. The host subsystem, e.g., configured to deliver pacing pulses and/or defibrillation shocks, includes a host controller (e.g., a processor) and a host power supply (e.g., a battery) to provide power for the host controller and other host components. The sensor subsystem, e.g., configured to obtain hemodynamic data and/or physiologic data, includes a sensor module, a sensor controller (separate from the host controller) to interact with sensor module, and a sensor power supply (separate from the host power supply) to provide power for the sensor module, the sensor controller and other components of the sensor subsystem. Assuming the host subsystem is part of a preexisting and already tested and approved type of implantable device (which may or may not include its own separate sensor circuitry), by keeping the host subsystem and the sensor subsystem electrically isolated from one another, the sensor subsystem's effect on the conventional functions of the host subsystem is reduced, and hopefully minimized. This is accomplished because operation of the sensor subsystem does not affect the host subsystem. Stated another way, a malfunction of the sensor subsystem does not affect the host subsystem. In this manner, the present invention provides for a quicker and less expensive way for the sensor subsystem to be added to the implantable device. The host subsystem and the sensor subsystem are also likely physically isolated from one another (e.g., they may be located on either side of a plane).

In accordance with an embodiment of the present invention, the implantable device includes a hermetically sealed container defining an interior region within which are located both the host subsystem and the sensor subsystem. Such a container likely includes a first container half and a second container half configured to be sealed to one another. In accordance with an embodiment of the present invention, the first container half was originally designed to be sealed to an original (i.e., different) second container half for the purpose of encapsulating only the host subsystem. However, in accordance with an embodiment of the present invention, the second container half is designed such that when it is sealed to the first container half, the sensor subsystem can be placed within the interior region of the sealed container without altering the original layout of the host subsystem. This can be accomplished by making the second container half deeper (i.e., more voluminous) than the first container half, and more importantly, deeper than the original second container half that was designed to be sealed to the first container half for the purpose of encapsulating only the host subsystem. Examples of the types of sensors that might be part of the sensor module of the sensor subsystem, include, but are not limited to: a photoplethysmography sensor, a temperature transducer, an ultrasound transducer, an acoustic sensor, an electrochemical sensor, an electrode to measure electrical activity of the heart, an activity sensor, and/or a posture sensor. Depending on what type of sensor(s) is/are incorporated into the sensor module, the second container half may include one or more sensor block, sensor window and/or sensor well.

In accordance with an embodiment of the present invention, the implantable device also includes a header configured to accept leads that interface with a portion of the host subsystem, as well as a separate header configured to accept leads that interface with a portion of the sensor subsystem.

The host subsystem will likely also include a host memory and a host telemetry circuit that is configured to transmit data from at least one of the host memory and the host controller to an external device. In accordance with an embodiment of the present invention, the sensor subsystem also includes a sensor memory (separate from the host memory) and a sensor telemetry circuit (separate from the host telemetry circuit) configured to transmit data from at least one of the sensor memory and the sensor controller to an external device.

In accordance with alternative embodiments of the present invention, rather than completely isolating the host subsystem and the sensor subsystem, there is some sharing of components (i.e., the sensor subsystem will use one or more components of the host subsystem). For example, the sensor subsystem can be powered by the host power supply. For another example, the sensor controller can be configured to store sensor data in the host memory. Additionally, the host telemetry circuit can be used to transmit data, which was stored in the host memory by the sensor controller, to an external device. In another embodiment, sensor data can be transmitted to an external device directly from the sensor controller or sensor memory using the host telemetry circuit.

In accordance with alternative embodiments of the present invention, a first hermetically sealed container defines an interior region within which is located the host subsystem, and a second hermetically sealed container (separate from the first container) defines an interior region within which is located the sensor subsystem. In such embodiments, the second container is attached to the separate first container such that the first and second containers can be implanted in a patient as a single implant. The first and second containers can be welded together. Alternatively, the first and second containers can be removably attached to one another (e.g., using screws), thereby enabling the second container (and the sensor subsystem therein) to be detached from the first container and explanted from a patient while leaving the first container (and the host subsystem therein) implanted in the patient.

Other embodiment, features and advantages of the invention will appear from the following description in which the preferred embodiments have been set forth in detail, in conjunction with the accompanying drawings and claims.

BRIEF DESCRIPTION OF THE FIGURES

FIG. 2B is a simplified block diagram showing additional details of the exemplary multi-chamber implantable stimulation device of FIG. 2A.

DETAILED DESCRIPTION OF THE INVENTION

While the data obtained from implanted sensors may be used by an implanted cardiac device for arrhythmia discrimination, pacing optimization, or the like, such sensor data is often valuable even if it is not used immediately by the implantable device. For example, such sensor data can be stored within the device and then telemetered to an external device which can display the data to a physician and/or analyze the data.

Embodiments of the present invention enable additional sensing hardware to be added to an implantable device (e.g., a cardiac stimulation device) more quickly and less expensively, with little or no affect on the conventional functions of the implantable device.

Figure 1A:
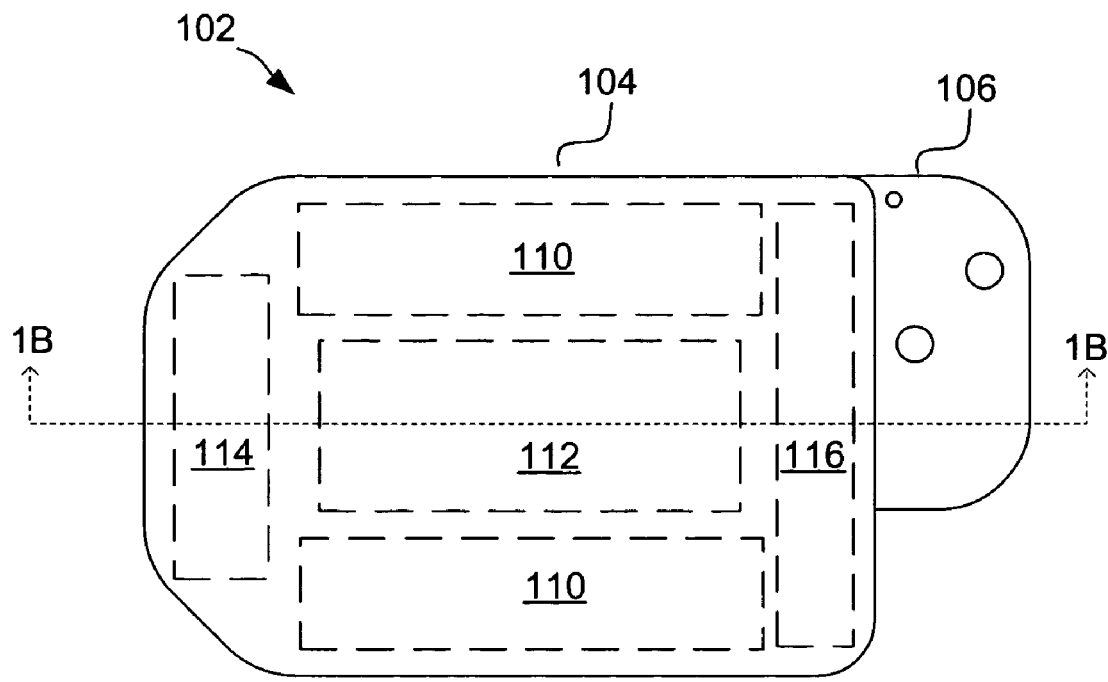
FIG. 1A illustrates a plan view of an exemplary implantable cardiac stimulation device.
Figure 1B:
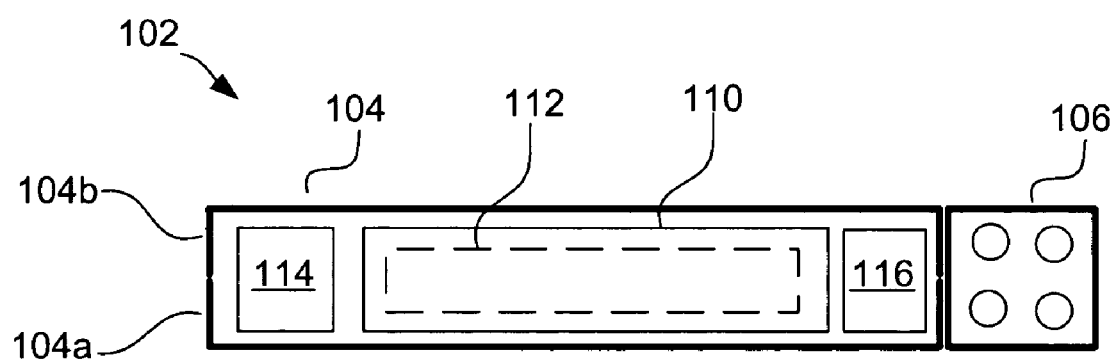
FIG. 1B illustrates a cross section of the device of FIG. 1A.

Referring to FIGS. 1A and 1B, an exemplary implantable cardiac stimulation device 102 is shown. The device 102, which may be an ICD, pacemaker or other stimulation device, includes a container housing 104 (also known as a "can") and a header 106 (also known as a "connector"). Housed within the container 104 are internal components including, e.g., a pair of charge capacitors 110, a battery 112, a low voltage electronics module 114 and a high voltage electronics module 116. The battery 112 is used to charge the capacitors 110, as well as to power the electronics modules 114 and 116.

Each of the electronics modules 114 and 116 can be, e.g., a hybrid circuit module that may contain multi-level circuit structures. The high voltage electronics module 116 may operate to deliver higher high-voltage pulses to a patient, typically on the order of 500-750 Volts. Before a high-voltage discharge occurs, the battery 112 first charges a discharge capacitor assembly including the capacitors 110. In response to a cardiac arrhythmia of a host patient, the capacitors 110 are discharged through the high voltage module 116. The electric discharge is transferred to the heart of a patient via stimulus leads connected to the header 116.

The low voltage electronics module 114 can include a control module which performs, e.g., cardiac pacing and sensing functions for sensing tachycardias, controlling pacing, determining when a high voltage discharge is warranted, etc. Accordingly, the low voltage module 114 will typically include a microcontroller unit (MCU), which is likely a microprocessor, and a memory for storing sensed data, tables, etc. The low voltage module 114 will likely also include a transmitter/receiver, also known as a telemetric circuit, for transmitting data to and receiving data from an external device (e.g., in a physician's office). Examples of telemetry circuits are discussed below.

Referring specifically to FIG. 1B, the container 104 consists of a bottom container half 104a and a container top half 104b (also referred to as bottom can half 104a and top can half 104b). Preferably, the container halves 104a and 104b are constructed of a biocompatible material, such as, but not limited to, titanium. During manufacture, after the internal components are placed in the bottom container half 104a, the container top half 104b is placed over the bottom container half 104a and hermetically sealed thereto, typically using laser welding or the like.

As mentioned above, if additional sensor hardware is to be added to the implantable cardiac stimulation device 102 it is important that the additional sensor hardware does not compromise the conventional functions (e.g., pacing, shocking, etc.) of the implantable stimulation device 102. Because invasive surgery is required each time the battery 112 needs to be replaced, it is also important that the power requirements of the additional sensor hardware do not reduce the life of the battery 112 to an unacceptable level. Additionally, it is important that the processing and storing of the sensor data associated with the additional sensing hardware does not compromise the processing and storing of data associated with pacing and/or shocking the patient. Further, attempting to integrate additional sensor hardware into the existing container housing 104 may necessitate redesigning the layout of the internal components (e.g., 110, 112, 114 and 116) in order to accommodate the volume occupied by the additional sensor hardware. Further, providing signal connections, data management, and telemetry for the additional sensor hardware will typically require changes to the device electronics 114 and/or 116, software and/or firmware. There are also further burdens to Quality Assurance to verify that the additional sensor hardware does not compromise the conventional functions of the implantable device 102.

As will be explained below, embodiments of the present invention overcome some, and preferably all, of the above mentioned disadvantages associated with integrating additional sensor hardware into an implanted cardiac stimulation device (e.g., device 102). More specifically, embodiments of the present invention provide for quicker and less expensive integration of additional sensing hardware into implantable devices. Further, embodiments of the present invention reduce, and preferably minimize, the effects on the conventional functions of the implantable devices. However, before explaining the present invention, it would be useful to first provide details of an exemplary implantable stimulation device 102.

Exemplary Details of an Implantable Stimulation Device

Figure 2A:
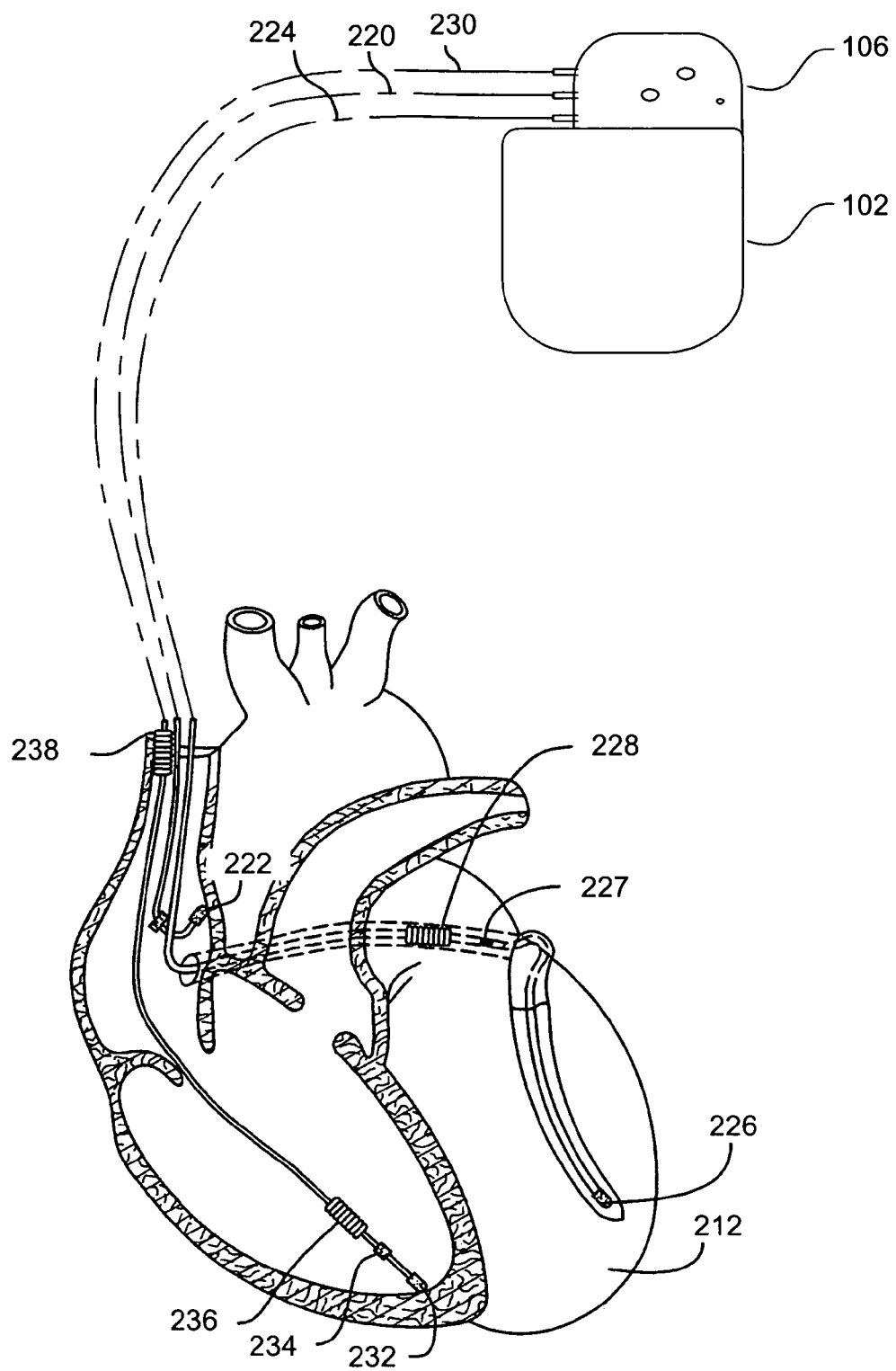
FIG. 2A illustrates an exemplary implantable stimulation device in electrical communication with a patient's heart by way of three leads, which are suitable for delivering multi-chamber stimulation and shock therapy.

Referring to FIG. 2A, the exemplary implantable stimulation device 102 is shown as being in electrical communication with a patient's heart 212 by way of three leads, 220, 224 and 230, suitable for delivering multi-chamber stimulation and/or shock therapy. To sense atrial cardiac signals and to provide right atrial chamber stimulation therapy, the stimulation device 102 is coupled to an implantable right atrial lead 220 having at least an atrial tip electrode 222, which typically is implanted in the patient's right atrial appendage.

To sense left atrial and ventricular cardiac signals and to provide left-chamber pacing therapy, the host stimulation device 102 is coupled to a "coronary sinus" lead 224 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

The exemplary coronary sinus lead 224 is designed to receive atrial and ventricular cardiac signals and to deliver left ventricular pacing therapy using at least a left ventricular tip electrode 226, left atrial pacing therapy using at least a left atrial ring electrode 227, and shocking therapy using at least a left atrial coil electrode 228.

The stimulation device 102 is also shown in electrical communication with the patient's heart 212 by way of an implantable right ventricular lead 230 having, in this embodiment, a right ventricular tip electrode 232, a right ventricular ring electrode 234, a right ventricular (RV) coil electrode 236, and an SVC coil electrode 238. Typically, the right ventricular lead 230 is transvenously inserted into the heart 212 so as to place the right ventricular tip electrode 232 in the right ventricular apex so that the RV coil electrode 236 will be positioned in the right ventricle and the SVC coil electrode 238 will be positioned in the superior vena cava. Accordingly, the right ventricular lead 230 is capable of receiving cardiac signals and delivering stimulation in the form of pacing and shock therapy to the right ventricle.

As illustrated in FIG. 2B, a simplified block diagram is shown of the multi-chamber implantable stimulation device 102, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation. Exemplary details of the low voltage electronics module 114 and the high voltage electronics module 116 are shown. For simplicity, the battery 112 is shown as being generally connected to modules 114 and 116, while in reality the batter 112 may be directly connected to individual blocks within the modules 114 and 116. Additionally, for simplicity, the capacitors 110 is shown as being generally connected to module 116, while it is more likely connected to specific blocks within the module 116. Elements are not drawn to scale.

The housing 104 for the stimulation device 102, shown schematically in FIG. 2B, (often referred to as the "can", "case" or "case electrode") may be programmably selected to act as the return electrode for all "unipolar" modes. The housing 104 may further be used as a return electrode alone or in combination with one or more of the coil electrodes, 228, 236 and 238, for shocking purposes. The housing 104 further includes a connector (not shown) having a plurality of terminals, 242, 244, 246, 248, 252, 254, 256, and 258 (shown schematically and, for convenience, the names of the electrodes to which they are connected are shown next to the terminals). As such, to achieve right atrial sensing and pacing, the connector includes at least a right atrial tip terminal ($A_R$ TIP) 242 adapted for connection to the atrial tip electrode 222.

To achieve left chamber sensing, pacing and shocking, the connector includes at least a left ventricular tip terminal ($V_L$ TIP) 244, a left atrial ring terminal ($A_L$ RING) 246, and a left atrial shocking terminal ($A_L$ COIL) 248, which are adapted for connection to the left ventricular tip electrode 226, the left atrial ring electrode 227, and the left atrial coil electrode 228, respectively.

To support right chamber sensing, pacing and shocking, the connector further includes a right ventricular tip terminal ($V_R$ TIP) 252, a right ventricular ring terminal ($V_R$ RING) 254, a right ventricular shocking terminal ($R_V$ COIL) 256, and an SVC shocking terminal (SVC COIL) 258, which are adapted for connection to the right ventricular tip electrode 232, right ventricular ring electrode 234, the RV coil electrode 236, and the SVC coil electrode 238, respectively. At the core of the stimulation device 102 is a programmable controller 260 which controls the various modes of stimulation therapy, including pacing optimization and anti-arrhythmia therapy. As is well known in the art, the controller 260 typically includes a microprocessor, or equivalent control circuitry, designed specifically for controlling the delivery of stimulation therapy and can further include RAM or ROM memory, logic and timing circuitry, state machine circuitry, and I/O circuitry. Typically, the controller 260 includes the ability to analyze signals (data) as controlled by a program code stored in a designated block of memory. The details of the design of the controller 260 are not critical to the present invention. Rather, any suitable controller 260 can be used to carry out the functions described herein. The use of microprocessor-based control circuits for performing timing and data analysis functions are well known in the art. In specific embodiment of the present invention, the controller 260 performs some or all of the steps associated with detecting specific events, triggering sampling, monitoring mean arterial pressure, pacing interval optimization and selecting an appropriate anti-arrhythmia therapy. It is noted that the controller 260 and microprocessor can be one in the same, or separate, depending on implementation and embodiment.

Representative types of control circuitry that may be used with the invention include the microprocessor-based control system of U.S. Pat. No. 4,940,052 (Mann et. al.) and the state-machines of U.S. Pat. No. 4,712,555 (Sholder) and U.S. Pat. No. 4,944,298 (Sholder). For a more detailed description of the various timing intervals used within the stimulation device and their inter-relationship, see U.S. Pat. No. 4,788,980 (Mann et. al.). The '052, '555, '298 and '980 patents are incorporated herein by reference.

As shown in FIG. 2B, an atrial pulse generator 270 and a ventricular pulse generator 272 generate pacing stimulation pulses for delivery by the right atrial lead 220, the right ventricular lead 230, and/or the coronary sinus lead 224 via an electrode configuration switch 274. It is understood that in order to provide stimulation therapy in each of the four chambers of the heart, the atrial and ventricular pulse generators, 270 and 272, may include dedicated, independent pulse generators, multiplexed pulse generators, or shared pulse generators. The pulse generators, 270 and 272, are controlled by the controller 260 via appropriate control signals, 276 and 278, respectively, to trigger or inhibit the stimulation pulses.

The controller 260 further includes timing control circuitry 279 which is used to control pacing parameters (e.g., the timing of stimulation pulses) as well as to keep track of the timing of refractory periods, PVARP intervals, noise detection windows, evoked response windows, alert intervals, marker channel timing, etc., which is well known in the art. Examples of pacing parameters include, but are not limited to, atrio-ventricular delay, interventricular delay and interatrial delay.

The switch bank 274 includes a plurality of switches for connecting the desired electrodes to the appropriate I/O circuits, thereby providing complete electrode programmability. Accordingly, the switch 274, in response to a control signal 280 from the controller 260, determines the polarity of the stimulation pulses (e.g., unipolar, bipolar, combipolar, etc.) by selectively closing the appropriate combination of switches (not specifically shown) as is known in the art.

Atrial sensing circuits 282 and ventricular sensing circuits 284 may also be selectively coupled to the right atrial lead 220, coronary sinus lead 224, and the right ventricular lead 230, through the switch 274 for detecting the presence of cardiac activity in each of the four chambers of the heart. Accordingly, the atrial (ATR. SENSE) and ventricular (VTR. SENSE) sensing circuits, 282 and 284, may include dedicated sense amplifiers, multiplexed amplifiers, or shared amplifiers. The switch 274 determines the "sensing polarity" of the cardiac signal by selectively closing the appropriate switches, as is also known in the art. In this way, the clinician may program the sensing polarity independent of the stimulation polarity.

Each sensing circuit, 282 and 284, preferably employs one or more low power, precision amplifiers with programmable gain and/or automatic gain control, bandpass filtering, and a threshold detection circuit, as known in the art, to selectively sense the cardiac signal of interest. The automatic gain control enables the device 102 to deal effectively with the difficult problem of sensing the low amplitude signal characteristics of atrial or ventricular fibrillation.

The outputs of the atrial and ventricular sensing circuits, 282 and 284, are connected to the controller 260 which, in turn, are able to trigger or inhibit the atrial and ventricular pulse generators, 270 and 272, respectively, in a demand fashion in response to the absence or presence of cardiac activity, in the appropriate chambers of the heart. The sensing circuits, 282 and 284, in turn, receive control signals over signal lines, 286 and 288, from the controller 260 for purposes of measuring cardiac performance at appropriate times, and for controlling the gain, threshold, polarization charge removal circuitry (not shown), and timing of any blocking circuitry (not shown) coupled to the inputs of the sensing circuits, 282 and 284.

For arrhythmia detection, the device 102 utilizes the atrial and ventricular sensing circuits, 282 and 284, to sense cardiac signals to determine whether a rhythm is physiologic or pathologic. The timing intervals between sensed events (e.g., P-waves, R-waves, and depolarization signals associated with fibrillation which are sometimes referred to as "F-waves" or "Fib-waves") are then classified by the controller 260 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to assist with determining the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 290. The data acquisition system 290 is configured to acquire intracardiac electrogram signals, convert the raw analog data into a digital signal, and store the digital signals for later processing and/or telemetric transmission to an external device 202. The data acquisition system 290 is coupled to the right atrial lead 220, the coronary sinus lead 224, and the right ventricular lead 230 through the switch 274 to sample cardiac signals across any pair of desired electrodes.

Advantageously, the data acquisition system 290 can be coupled to the controller 260, or other detection circuitry, for detecting an evoked response from the heart 212 in response to an applied stimulus, thereby aiding in the detection of "capture". Capture occurs when an electrical stimulus applied to the heart is of sufficient energy to depolarize the cardiac tissue, thereby causing the heart muscle to contract. The controller 260 detects a depolarization signal during a window following a stimulation pulse, the presence of which indicates that capture has occurred. The controller 260 enables capture detection by triggering the ventricular pulse generator 272 to generate a stimulation pulse, starting a capture detection window using the timing control circuitry 279 within the controller 260, and enabling the data acquisition system 290 via control signal 292 to sample the cardiac signal that falls in the capture detection window and, based on the amplitude, determines if capture has occurred.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al.); and U.S. Pat. No. 5,350,410 (Mann et. al.), which patents are hereby incorporated herein by reference. The type of capture detection system used is not critical to the present invention.

The controller 260 is further coupled to a memory 294 by a suitable data/address bus 296, wherein the programmable operating parameters used by the controller 260 are stored and modified, as required, in order to customize the operation of the stimulation device 102 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 212 within each respective tier of therapy. The memory 294, or a further memory, can also be used to store homodynamic and/or physiologic data that is obtained by the device 102.

Advantageously, the operating parameters of the implantable device 102 may be non-invasively programmed into the memory 294 through a telemetry circuit 201 in telemetric communication with the external device 202, such as a programmer, transtelephonic transceiver, or a diagnostic system analyzer. The telemetry circuit 201 is activated by the controller 260 by a control signal 206. The telemetry circuit 201 advantageously allows intracardiac electrograms and status information relating to the operation of the device 102 (as contained in the controller 260 or memory 294) to be sent to an external device 202 through an established communication link 204.

Examples of telemetry circuits are described in the following U.S. patents, each of which is incorporated herein by reference: U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734, entitled "Efficient Generation of Sensing Signals in an Implantable Medical Device such as a Pacemaker or ICD" (note: this patent relates to transfer of EGM data) (Mc-Clure et al.). Another example of a telemetric circuit for use in a chronically implantable device is the TR1000 transceiver manufactured by RF Monolithics, Dallas, Tex. The TR 1000 is a single-chip, low-power, 916.5 MHz transceiver. An operating frequency of about 916.5 MHz is typically desirable because of the modest requirements on antenna size it imposes. Such telemetry circuits can use, e.g., magnetic induction, radio telemetry or acoustic telemetry.

In accordance with an embodiment, the stimulation device 102 further includes one or more host physiologic sensors 208, that can be used to obtain physiologic data.

The battery 112 provides operating power to all of the circuits shown in FIG. 2B. If the stimulation device 102 employs shocking therapy, the battery 112 should be capable of operating at low current drains for long periods of time, and then be capable of providing high-current pulses (for capacitor charging) when the patient requires a shock pulse. The battery 112 should also have a predictable discharge characteristic so that elective replacement time can be detected. Accordingly, the device 102 preferably employs lithium/silver vanadium oxide batteries, as is true for most (if not all) current devices, but is not limited thereto.

The stimulation device 102 can also includes a magnet detection circuitry (not shown), coupled to the controller 260. It is the purpose of the magnet detection circuitry to detect when a magnet is placed over the stimulation device 102, which magnet may be used by a clinician to perform various test functions of the stimulation device 102 and/or to signal the controller 260 that the external programmer 202 is in place to receive or transmit data to the controller 260 through the telemetry circuits 201.

As further shown in FIG. 2B, the device 102 is shown as having an impedance measuring circuit 213 which is enabled by the controller 260 via a control signal 214. The known uses for an impedance measuring circuit 213 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; measuring thoracic impedance for detecting and assessing the severity of pulmonary edema; detecting when the device has been implanted; measuring stroke volume; and detecting the opening of heart valves, etc. The impedance measuring circuit 213 is advantageously coupled to the switch 274 so that any desired electrode may be used. In addition, to facilitate the measurement of peripheral tissue edema, extra electrodes can be added to the device housing, thereby limiting the test electric field to the peripheral tissue.

In the case where the stimulation device 102 is alternative or additionally intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the controller 260 further controls a shocking circuit 216 by way of a control signal 218. The shocking circuit 216 generates shocking pulses of low (up to 0.5 Joules), moderate (0.5-10 Joules), or high energy (11 to 40 Joules), as controlled by the controller 260. Such shocking pulses are applied to the patient's heart 212 through at least two shocking electrodes, and as shown in this embodiment, selected from the left atrial coil electrode 228, the RV coil electrode 236, and/or the SVC coil electrode 238. As noted above, the housing 104 may act as an active electrode in combination with the RV electrode 236, or as part of a split electrical vector using the SVC coil electrode 238 or the left atrial coil electrode 228 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 Joules), delivered asynchronously (since R-waves may be too disorganized to be recognize), and pertaining exclusively to the treatment of fibrillation. Accordingly, the controller 260 is capable of controlling the synchronous or asynchronous delivery of the shocking pulses. Another approach to electrical anti-arrhythmia therapy is anti-tachycardia pacing, in which low-voltage pacing pulses are applied to pace-terminate the arrhythmia. This approach is particularly effective in low rate ventricular tachycardias.

Additional and alternative details of implantable cardiac stimulation devices can be found in U.S. Pat. No. 5,405,363

(Kroll et al.) and U.S. Pat. No. 5,040,534 (Mann et al.), both of which are incorporated herein by reference.

Now that an exemplary cardiac stimulation device has been described, embodiments of the present invention will be described in more detail.

Autonomous Additional Sensor Components

Figure 3:
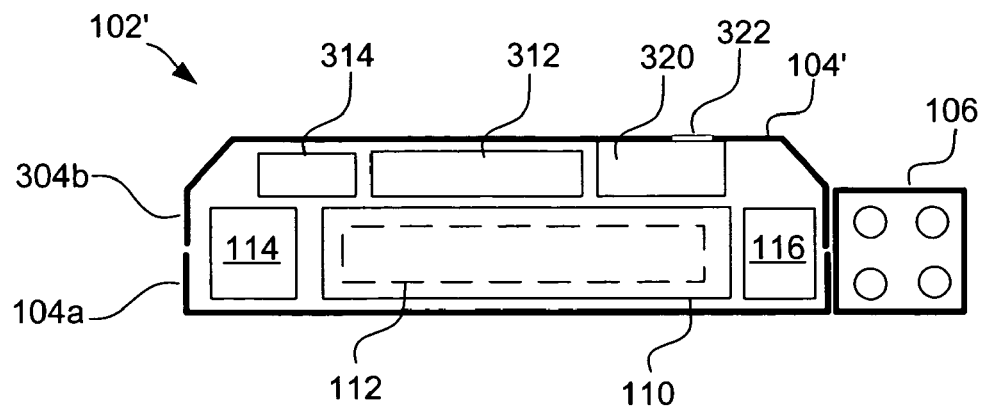
FIG. 3 illustrates the device of FIGS. 1A and 1B modified in accordance with an embodiment of the present invention.

Specific embodiments of the present invention will first be discussed with reference to FIG. 3. Referring to FIG. 3, in accordance with an embodiment of the present invention, a deeper (i.e., wider) container top half 304b is used in place of the host device's container top half 104b (of FIG. 1B), such that when the deeper container top half 304b is sealed to the host device's bottom container half 104a it provides for a modified container 104' with a larger internal volume. Preferably the deeper container top half 304b has the same circumferential shape as the host device's container top half 104b that it is replacing, thereby allowing for easy substitution. (The term "host" is used here because in many embodiments it is as if the additional sensor components are being hosted by a housing originally designed only for the components of the "host" device 102.) Because of the larger internal volume, the modified container 104' (resulting from the deeper container top half 304b) can store more components therein. Assuming that the host cardiac stimulation device 102 is a type of existing device that has already been tested, approved, and is being used in actual patients, the deeper container top half 304b can be used to easily add additional sensor hardware to the already existing cardiac stimulation device 102. More specifically, the additional internal volume that is obtained by using the deeper container half 304b in place of the host container half 104b enables the modified housing 104' to accommodate one or more sensors and associated sensor electronics without necessitating redesigning the layout of the original internal components (e.g., components 110, 112, 114 and 116). It is also possible to produce a modified housing a deeper bottom container half (in place of the host bottom container half 104a) together with the host top half 104b.

Referring to FIG. 3, the modified device (designated 102') includes additional sensor components represented as blocks, with block 320 representing a sensor module, block 312 representing a further battery, and block 314 representing sensor control electronics. In the embodiment of FIG. 3, the sensor module 320 is a leadless sensor module, and thus does not require a header (also known as a "connector"). However, as will be described below with reference to FIG. 5, an additional header may be added if the sensor module 320 being added to the host device requires one or more lead.

Referring to the embodiment of FIG. 3, the substitute container top half 304b can include one or more sensor window 322 sensor block and/or sensor well. In accordance with an embodiment of the present invention, the sensor module 320 includes a photoplethysmography (PPG) sensor, which includes a light source (e.g., one or more light emitting diode) and a light detector. For such an embodiment, the container top half 304b may include an optical window through which light can be transmitted and received. Alternatively, a light source and a light detector may be placed in separate wells that can be machined, formed or cast in the container top half 304b. Preferably, each well and is formed using the minimum volume necessary to contain its feed-through connector and optical device. Locating the source and detector in separate wells ensures that no light passes directly between them. In still another embodiment, the source and detector are placed in the same well with an opaque barrier placed between them. The remaining space in the well can be filled with an epoxy such that the outer surface of the container top half 304b is smooth and flat, thereby minimizing the risk of tissue trauma and infection. The light source and detector can be connected via feed-through connections to the sensor control electronics 314, thus ensuring hermeticity. Placing the optical components in wells thus enhances optical isolation while maintaining hermeticity. Alternatively, a light source and a light detector (or other sensor module) may be placed in a separately manufactured sensor block which is subsequently integrated into the container top half 304b, e.g., by laser-welding the sensor block to the container top half 304b. Additional details of including a PPG sensor in an implantable device are provided in commonly assigned U.S. patent application Ser. No. 10/764,419, filed Jan. 23, 2004, entitled "Using Photo-Plethysmography to Monitor Autonomic Tone and Performing Pacing Optimization based on Monitored Autonomic Tone," which is incorporated herein by reference. It is also noted that in an embodiment in which the sensor module 320 includes a light source, the light source can be used for telemetry, eliminating the need for a separate dedicated telemetry circuit.

In accordance with another embodiment, the sensor module 320 includes an acoustic sensor (also known as a sound sensor) that can be used to detect heart sounds. In still another embodiment, the sensor module 320 includes a temperature transducer for measuring body temperature. Other types of sensors that can be included in the sensor module include, but are not limited to, an ultrasound transducer, an impedance sensor, an electrochemical sensor (e.g., for detecting pH, $CO_2$, $pO_2$, $pCO_2$, etc.) and a motion/posture sensor (e.g., an accelerometer). The sensor module 320 can even include one or more electrodes that are used to measure electrical activity of the heart. The sensor module 320 can also include combinations of these and other types of sensors. Details of an exemplary acoustic sensor and an exemplary PPG sensor are provided in U.S. Pat. No. 6,477,406 entitled "Method for Monitoring Heart Failure" (Turcott) and U.S. Pat. No. 6,480,733 entitled "Extravascular Hemodynamic Acoustic Sensor" (Turcott), each of which is incorporate herein by reference. As is describe in these patents, a PPG sensor can be used for obtaining various types of information include arterial blood pressure and blood oxygen saturation levels (using pulse oximetry). Details of exemplary motion and posture sensors are provided in the following patents, each of which are incorporated herein by reference: U.S. Pat. No. 6,658,292, entitled "Detection of Patient's Position and Activity Status Using 3D Accelerometer-Based Position Sensor" (Kroll et al.); U.S. Pat. No. 6,466,821, entitled "Orientation of Patient's Position Sensor Using External Field" (Kroll et al.); and U.S. Pat. No. 6,625,493, entitled "AC/DC Multi-Axis Accelerometer for Determining Patient Activity and Body Position" (Pianca et al.).

Figure 4:
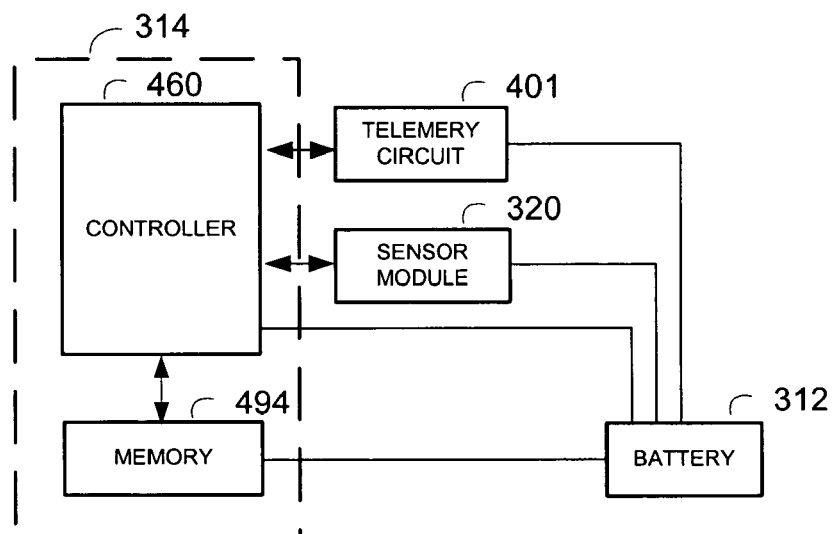
FIG. 4 illustrates exemplary details of the sensor control electronics shown in FIG. 3.

Exemplary details of the sensor control electronics 314 are shown in FIG. 4. Referring to FIG. 4, the sensor control electronics 314 can include a controller 460 (e.g., a microprocessor and/or other control circuitry), a memory 494, and the like, which are useful for controlling the sensor module 320 and storing sensor data obtained using the sensor module 320. A sensor specific telemetry circuit 401, which can be similar to the telemetry circuit 201 discussed above, can be used for transmitting data to and receiving data from an external device (e.g., in a physician's office).

Preferably, the additional sensor components including the sensor control electronics 314, the sensor battery 312 and the sensor telemetry circuit 401 are electronically isolated from the components associated with the host device 102. Stated another way, in this embodiment there are no electrical connections between the components associated with the host device 102 shown in FIGS. 1A and 1B and the added components associated with the additional sensor(s). Thus, there is no sharing of battery power, memory space, processing, etc. Such an embodiment significantly reduces the development time and effort required to add additional sensor functionality to an existing device, as compared to fully integrating the additional sensor(s). Furthermore, the risk of the additional sensor components interfering with the conventional functions of the host device 102 is essentially eliminated, thereby minimizing the work of Quality Assurance and simplifying the regulatory pathway. Such an approach is particularly attractive to early-stage sensor development, as well as in the testing of sensors whose long-term commercial viability has not yet been demonstrated. If desired, electromagnetic interference (EMI) shielding can be use to further isolate the additional sensor components from the host components.

Substantially Autonomous Additional Sensor Components

In accordance with alternative embodiments of the present invention, rather than completely isolating the host components and the additional sensor components, there is some sharing of components. More specifically, in accordance an embodiment of the present invention, the battery 112 of the host device is used to also power the components associated with the additional sensor(s). Thus, in such embodiments there is no need for the additional battery 312 shown in FIG. 3), thereby enabling the size of the substitute container top half 304b (and thus, the entire implant) to potentially be reduced. In this embodiment, the only electrical connection between the additional sensor components (e.g., sensor control electronics 314 and sensor module 320) and the host device components (e.g., components 112, 114 and 116) is between the additional sensor components and the host's battery 112. Such embodiments are feasible so long as the host's battery 112 can support the additional sensor components without adversely effecting the conventional functions of the host device 102, such as the charging of the capacitors 110. Additionally, the battery life should remain at an acceptable level so as to not significantly reduce the length of time between battery replacements. In such an embodiment, the development time and effort required to add additional sensor functionality to an existing device is still significantly reduced (as compared to fully integrating the additional sensor components) because there are still no signal connections from the sensor module 320 and sensor control electronics 314 to the control and data storage electronics (e.g., the low voltage module 114) of the host device 102. Furthermore, the risk of the sensor components interfering with the conventional functions of the host device 102 is still low since the only sharing is of the battery 112. Accordingly, while the work of Quality Assurance may be greater than the completely autonomous embodiment described above, where not even the battery is shared, it should still be relatively simple as compared to a device where the additional sensor components are fully integrated.

In accordance with still another embodiment of the present invention, the telemetry circuit 201 of the host device 102 is also used to transmit/receive data associated with the additional sensor module 320. Thus, in such embodiments there is no need for the additional telemetry circuit 401 shown in FIG. 4, thereby enabling the size of the substitute container top half 304b (and thus, the entire implant) to potentially be reduced.

In accordance with a further embodiment of the present invention, the memory 294 of the host device is also used to store sensor data associated with the additional sensor module 320. In such an embodiment, when the contents of the host memory 294 are telemetered to an external device (e.g., shown in FIG. 2A 2B as device 202) using the host's telemetry circuit 201, the sensor data obtained from the additional sensor module 320 will also be transmitted to the external device 202, and thus be available for external analysis. Accordingly, in such an embodiment, there is no need for the additional telemetry circuit 401.

In each of the above embodiments, it is preferable that the host controller 260 is not required to be aware (i.e., it is unaware) of the additional sensor hardware, thereby not requiring any modification to the software/firmware associated with the host controller 260. In summary, the additional sensor components can share one or more of the host device's battery 112, telemetry circuit 201 and memory 294. This is preferably accomplished without modifying the host controller 260, and without modifying the original layout of the host components.

Figure 5:
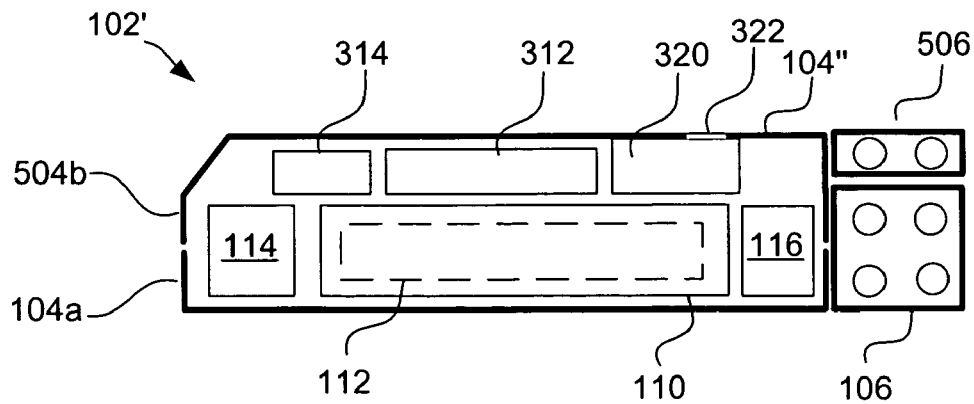
FIG. 5 illustrates the device of FIGS. 1A and 1B modified in accordance with another embodiment of the present invention that includes an additional header.

Referring now to FIG. 5, in accordance with an embodiment of the present invention, a deeper (i.e., wider) container top half 504b that is used in place of the host device's container top half 104b (of FIG. 1B) has a corresponding header 506 that provides connections for one or more sensor leads. This will enable leaded sensors, such as, but not limited to, a pressure transducer, and oxygen sensor and/or a cardio mechanical electrical sensor, to be added, without any modification to the host device's header 106. The headers 506 and 106 can in practice be manufactured and attached to the laser-welded device 102' as an integrated unit, or, as illustrated in FIG. 5, can be manufactured and attached separately. To minimize the risk of infection, space between the header(s) can be reduced and preferably eliminated by design and/or adding a filler material such as silicone.

Separate Additional Sensor Device

Figure 6A:
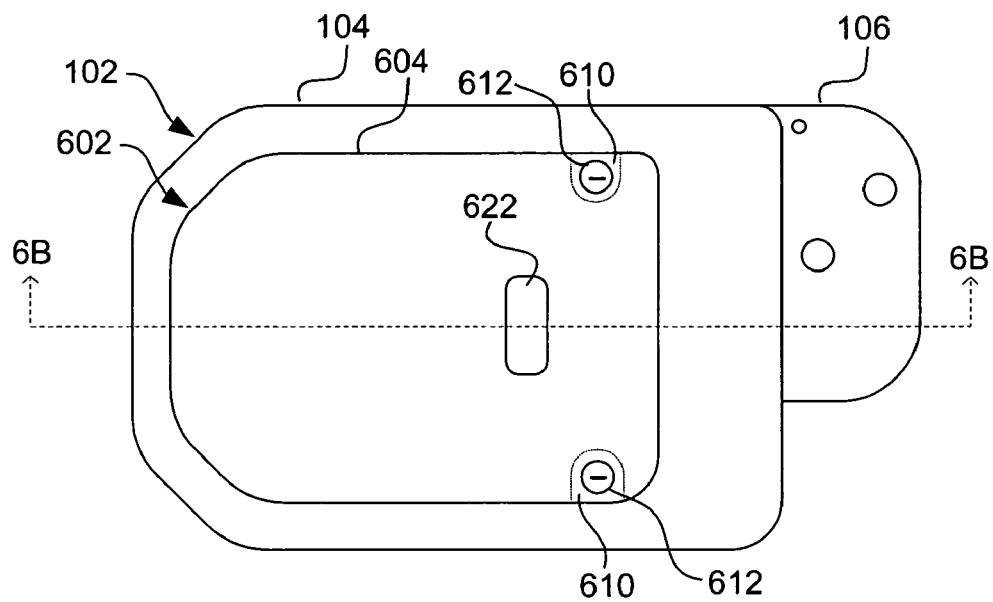
FIGS. 6A and 6B illustrates an embodiment of the present invention where a separate sensor housing is attached to an implantable stimulation device such as the one shown in FIGS. 1A and 1B.
Figure 6B:
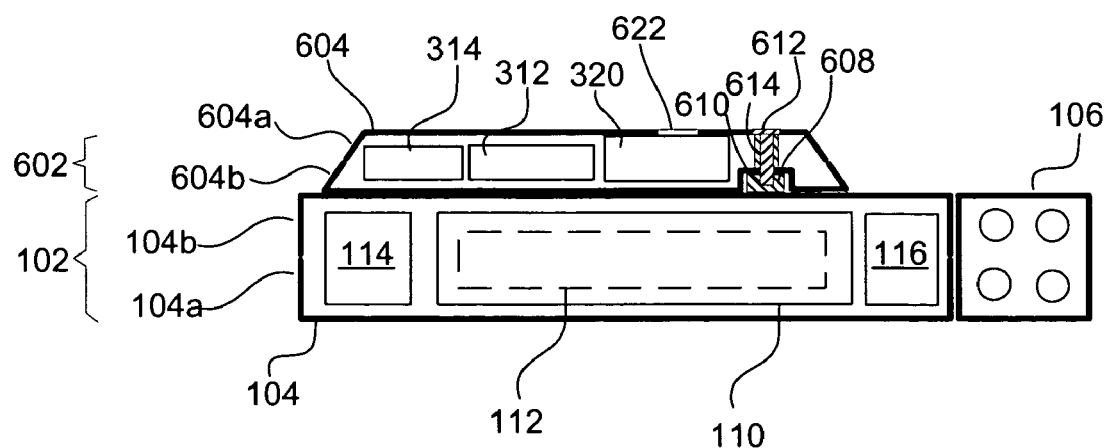

Referring now to FIGS. 6A and 6B, in accordance with further embodiments of the present invention, a separate sensor device 602 is attached to the host device 102. More specifically, in accordance with another embodiment of the present invention, the host device's container 104 (including container halves 104a and 104b) is used to encase the host components, while additional sensor hardware (e.g., the sensor module 320, the further battery 312 and the sensor control electronics 314) is encased in a separate container 604 that is attached to the host container 104. Similar to the host container 104, the separate sensor container 604 likely includes a bottom container half 604b and a container top half 604a. As with the embodiments discussed above with reference to FIG. 3, the container top half 604a of the separate sensor device 602 can include one or more sensor window 622, sensor block and/or sensor well. Although not required, it is preferred that the circumferential walls of the separate container 604 gently slope toward the host container 104 such that there are obtuse angles formed where the two housings meet, as shown in FIG. 6B. This reduces the chance that fluid will pool at the areas where the two containers 104 and 604 meet, thereby reducing the chances of bacteria growing in such areas.

In the embodiments of FIGS. 6A and 6B, the additional sensor components that are encased within the separate container 604 are physically and electrically isolated from the components of the host device 102. Thus, there is no sharing of battery power, memory space, processing, etc. Accordingly, such embodiments will also significantly reduce the development time and effort required to add additional sensor functionality to an existing implantable device, as compared to a fully integrated sensor. Furthermore, the risk of the sensor components interfering with the conventional function of the host device 102 is essentially eliminated, thereby minimizing the work of Quality Assurance and simplifying the regulatory pathway. Accordingly, this approach is also particularly attractive to early-stage sensor development, as well in the testing of sensors whose long-term commercial viability has not yet been demonstrated.

In accordance with further embodiments of the present invention, the separate container 604 is attached to the host device container 104 by permanently welding the separate container 604 to the host device container 104. In such an embodiment, the host device 102 would need to be removed from the patient wherever there is a desire or need to explant (i.e., remove) the separate container 604 and the components therein from the patient.

In accordance with an alternative embodiment of the present invention, the separate container 604 is removably attached to the host container 104. This can be accomplished by appropriately welding one or more bosses 610 (e.g., a width of metal with an internal tapped hole therein) to an external surface of the host container 104, e.g., using a welding fixture. Preferably, the portion of the separate container 604 that would be adjacent the host container 104 (e.g., the bottom container half 604b) has mating features that enable the separate container 604 to lock in place adjacent the host container 104. Sealed through holes 614 can extend through a dead space portion of the separate sensor device 602, thereby allowing one or more screws 612 to attach the separate container 604 to the host container 104. Additionally, the container top half 604a of the separate container 604 can have a counter-bore that allows the top of the screw head(s) to be flush with the outer surface of the container 604. A silicone seal can be applied to the screws 612, counter bores, and seam between host device container 104 and separate container 604 to minimize the risk of infection.

If there is ever a desire or need to explant (i.e. remove) the separate sensor device 602 while leaving the host device 102 implanted, the sensor device 602 can be unscrewed from the host device 102 during surgery. This provides for clinical convenience. Additionally, if desired, a further separate sensor device can replace the removed sensor device. Accordingly, the host device 102 and attached separate sensor device 602 are preferably implanted such that following implantation, the separate sensor device 602 faces the chest wall, thereby allowing for easier access for removing the separate sensor device 602.

Figure 7A:
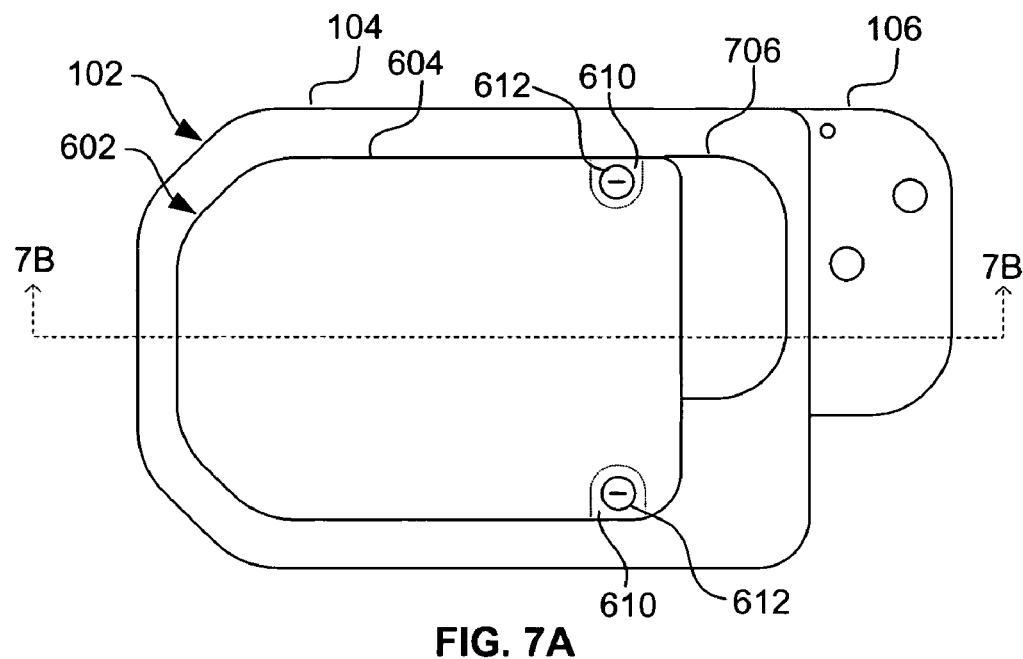
FIGS. 7A and 7B are similar to FIGS. 6A and 6B, but with the addition of a separate header for the separate sensor housing.
Figure 7B:
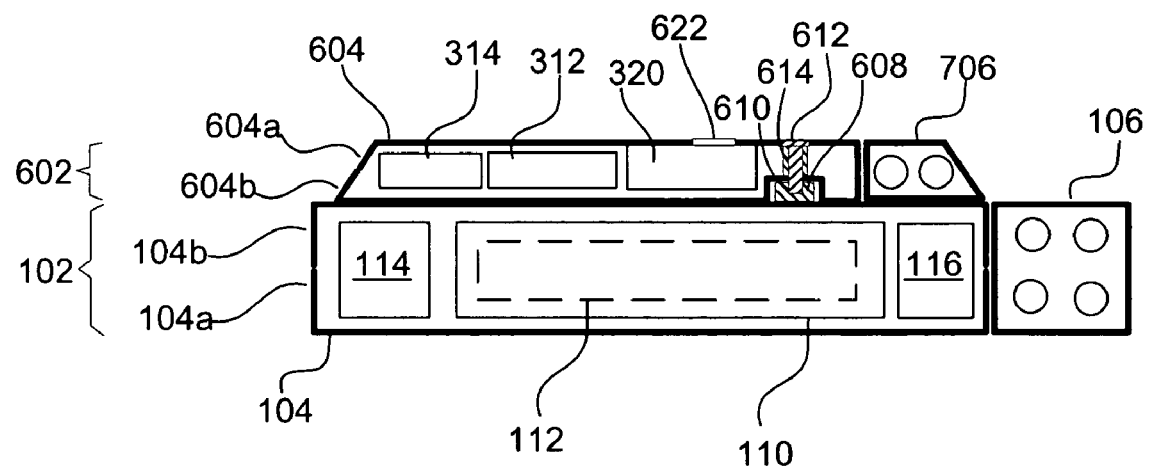
Figure 8:
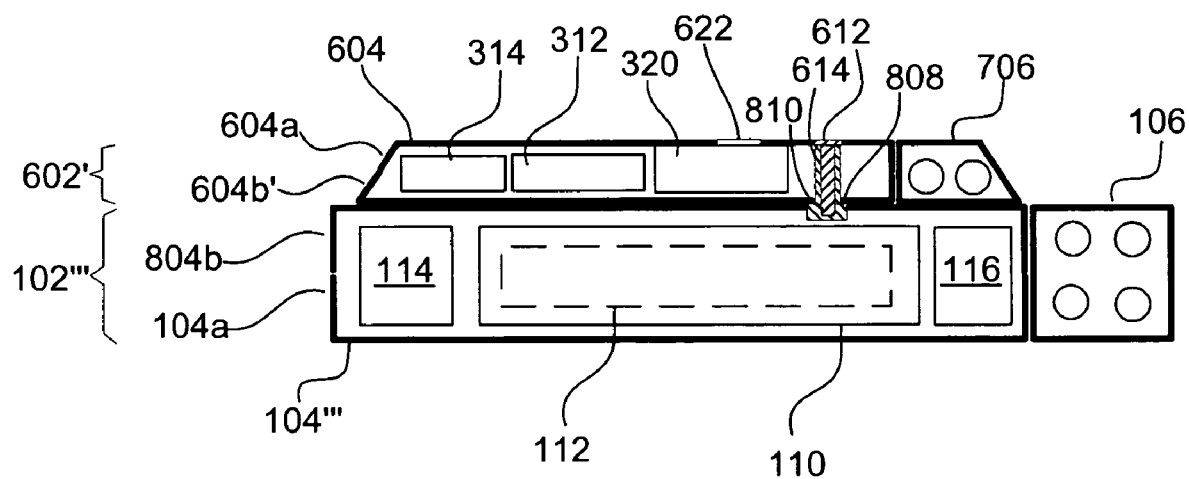
FIG. 8 illustrates an embodiment of the present invention where a separate sensor housing is attached to an implantable stimulation device, in accordance with another embodiment of the present invention.

In the embodiment of FIGS. 6A and 6B, the sensor module 320 is shown as a leadless sensor module, and thus does not require a header (i.e., connector). In accordance with another embodiment, shown in FIGS. 7A and 7B, the separate sensor device 602 can have a corresponding header 706 that provides connections for one or more sensor leads. This will enable leaded sensors, such as, but not limited to, a pressure transducer, and oxygen sensor and/or a cardio mechanical electrical sensor, to be added.

In accordance with still another embodiment of the present invention, a container half 804b that includes one or more bosses 808 and machined tapped holes 810 is used in place of the host device's container top half 104b (of FIG. 1B), to form a modified container 104'''. Such a replacement top half 804b will allow the separate sensor device 602' (similar to separate sensor device 602) to be more easily connected by one or more screws 612 to the modified host device 102'''. If desired, the separate sensor device 602' can have a corresponding additional header 706 that provides connections for one or more sensor leads.

One of ordinary skill in the art will appreciate that the separate sensor device 602 can be attached to the host device 102 in other manners than those described above, while still being within the spirit and scope of the present invention.

Figure 9:
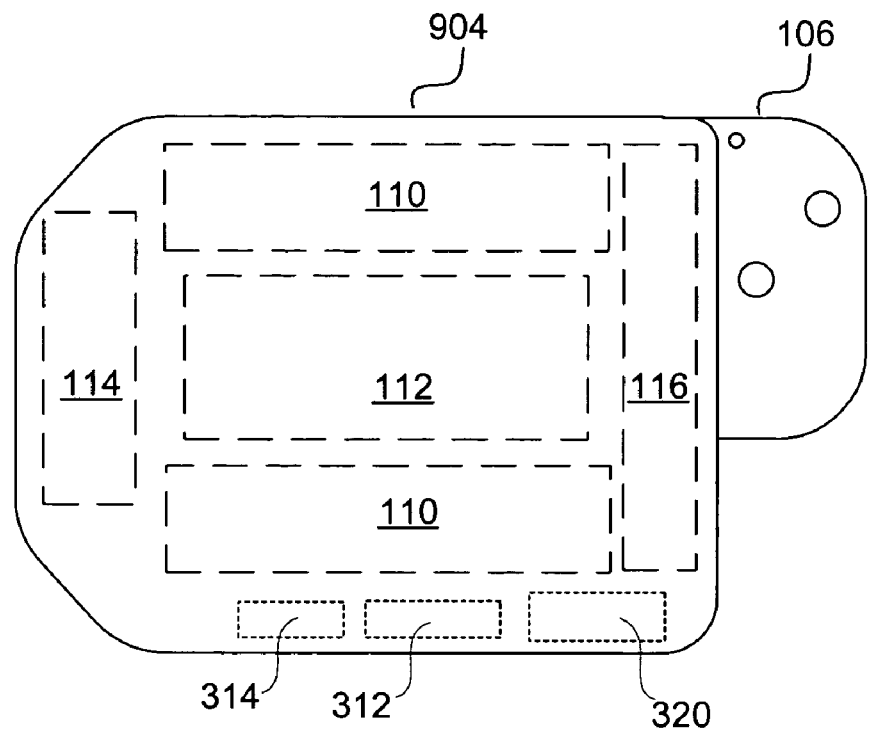
FIGS. 9 and 10 illustrate alternative embodiments where larger containers are used to house both a host subsystem and a sensor subsystem.
Figure 10:
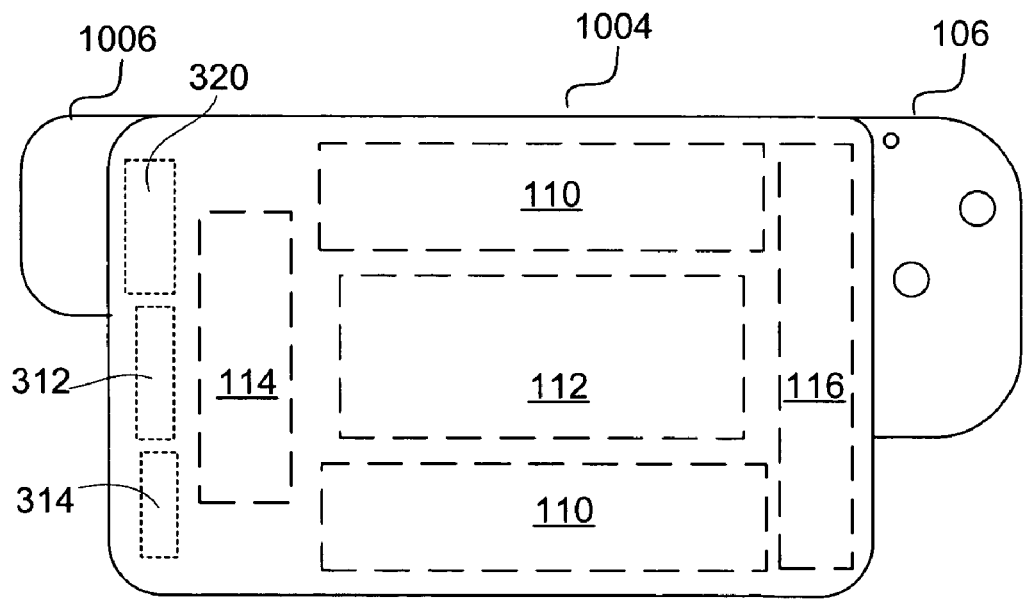

As shown in FIGS. 9 and 10, in accordance with further embodiments of the present invention, rather than making a modified container that is deeper than the container originally designed for the host device, the host container 104 is replaced with a larger housing 904 or 1004 that allows the sensor components (e.g., 312, 314 and 320) to fit within the housing. As shown in FIG. 10, a separate header 1006 for the sensor module 320 can be added, e.g., at an opposite end of the housing 1004 as the host header 106.

CONCLUSION

While the host device 102 has been described above as being a cardiac stimulation type device (e.g., for pacing and/or shocking the heart), it is also possible that the host device is primarily a monitoring type device that does not deliver any type of stimulation.

The previous description of the preferred embodiments is provided to enable any person skilled in the art to make or use the embodiments of the present invention. While the invention has been particularly shown and described with reference to preferred embodiments thereof, it will be understood by those skilled in the art that various changes in form and details may be made therein without departing from the spirit and scope of the invention.

What is claimed is:

1. An implantable device, comprising:
    a host subsystem including
        a host controller;
        a host sensor circuit configured to sense cardiac signals; and
        a host power supply to provide power for the host controller and host sensor circuit;
    a sensor subsystem coupled to the host subsystem, wherein the sensor subsystem is configured to obtain at least one of hemodynamic and physiologic data, the sensor subsystem including
        a sensor module;
        a sensor controller to interact with the sensor module, the sensor controller separate from the host controller; and
        a sensor power supply to provide power for the sensor module and the sensor controller, the sensor power supply separate from the host power supply;
    a hermetically sealed container defining an interior region within which are located both the host subsystem and the sensor subsystem, wherein the container includes a first container half and a second container half configured to be sealed to one another; and wherein
        the first container half is designed for the host subsystem;
        the second container half is designed to allow the sensor subsystem to be placed within the interior region of the container without altering a layout of the host subsystem; and
        the second container half comprises a sensor window.

2. An implantable device, comprising:
    a host subsystem including
        a host controller;
        a host sensor circuit configured to sense cardiac signals; and
        a host power supply to provide power for the host controller and host sensor circuit;
    a sensor subsystem coupled to the host subsystem, wherein the sensor subsystem is configured to obtain at least one of hemodynamic and physiologic data, the sensor subsystem including a sensor module;

a sensor controller to interact with the sensor module, the sensor controller separate from the host controller; and a sensor power supply to provide power for the sensor module and the sensor controller, the sensor power supply separate from the host power supply, a hermetically sealed container defining an interior region within which are located both the host subsystem and the sensor subsystem, wherein the container includes a first container half and a second container half configured to be sealed to one another; and wherein the first container half is designed for the host subsystem;

the second container half is designed to allow the sensor subsystem to be placed within the interior region of the container without altering a layout of the host subsystem; and the second container half comprises a sensor well.

3. An implantable device, comprising:

a host subsystem including:
  a host controller;
  a host memory;
  a host sensor circuit configured to sense cardiac signals;
  a host telemetry circuit configured to transmit data from at least one of the host memory and the host controller to an external device; and
  a host power supply to provide power for the host controller, the host memory the host sensor circuit and the host telemetry circuit;

a sensor subsystem electrically isolated from the host subsystem configured to obtain at least one of hemodynamic and physiologic data, including:
  sensor module;
  a sensor controller to interact with the sensor module, the sensor controller separate from the host controller; and
  a sensor power supply to provide power for the sensor module and the sensor controller, the sensor power supply separate from the host power supply;

a hermetically sealed container defining an interior region within which are located both the host subsystem and the sensor subsystem, wherein:
  the container includes a first container half and a second container half;
  the first container half is designed for the host subsystem; and
  the first container half having a volume;
  the second container half is designed for the sensor subsystem;
  the second container half having a volume larger than the volume of the first container half; and
  the second container half comprises a sensor well.

4. The device of claim 3, wherein:
the host power supply comprises a battery; and
the sensor power supply comprises a further battery.

5. The device of claim 3, wherein the sensor module of the sensor subsystem comprises at least one of the following:
a photoplethysmography sensor;
a temperature transducer;
an ultrasound transducer;
an acoustic sensor;
an electrochemical sensor;
an electrode to measure electrical activity of the heart;
an activity sensor; and
a posture sensor.

6. The device of claim 3, wherein the sensor subsystem further includes
a sensor memory; and
a sensor telemetry circuit configured to transmit data from at least one of the sensor memory and the sensor controller to an external device.

7. The device of claim 6, wherein the host subsystem further includes a capacitor to store charges useful for delivering defibrillation shocks and wherein the host power supply charges the capacitor.

8. The device of claim 3, further comprising:
a host header configured to accept leads that interface with a portion of the host subsystem; and
a sensor header, separate from the host header, configured to accept leads that interface with a portion of the sensor subsystem.

9. The device of claim 8, further comprising:
a header configured to accept host leads that interface with a portion of the host subsystem; and
sensor leads that interface with a portion of the sensor subsystem.

10. The device of claim 3, wherein the second container half comprises a sensor block within which the sensor module is located.

11. The device of claim 2 wherein the sensor subsystem further includes a sensor memory and wherein the sensor module comprises a light source configured to transmit data from at least one of the sensory memory and the sensor controller to an external device.

* * * * *

UNITED STATES PATENT AND TRADEMARK OFFICE
CERTIFICATE OF CORRECTION

PATENT NO.       : 7,653,434 B1
APPLICATION NO. : 10/913942
DATED            : January 26, 2010
INVENTOR(S)      : Turcott et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1050 days.

Signed and Sealed this

Twenty-third Day of November, 2010

David J. Kappos
*Director of the United States Patent and Trademark Office*